United States Patent
Greenwald et al.

(10) Patent No.: US 7,493,828 B2
(45) Date of Patent: Feb. 24, 2009

(54) SIMULATOR FOR EVALUATING ARTIFICAL JOINT SPECIMENS AND ASSOCIATED METHOD

(75) Inventors: A. Seth Greenwald, Cleveland Heights, OH (US); Paul D. Postak, University Heights, OH (US); Majid Rashidi, Pepper Pike, OH (US)

(73) Assignee: Orthopaedic Research Laboratories, Cleveland, OH (US)

( * ) Notice: Subject to any disclaimer, the term of this patent is extended or adjusted under 35 U.S.C. 154(b) by 66 days.

(21) Appl. No.: 11/498,313

(22) Filed: Aug. 2, 2006

(65) Prior Publication Data

US 2008/0033565 A1 Feb. 7, 2008

(51) Int. Cl.
*G01N 3/08* (2006.01)
(52) U.S. Cl. ....................................... 73/818
(58) Field of Classification Search ............ 73/760–856
See application file for complete search history.

(56) References Cited

U.S. PATENT DOCUMENTS

| | | | | |
|---|---|---|---|---|
| 3,790,965 | A * | 2/1974 | Gelbenegger | 623/38 |
| 5,417,693 | A * | 5/1995 | Sowden et al. | 606/85 |
| 6,564,647 | B1 * | 5/2003 | Richter et al. | 73/818 |
| 2002/0128715 | A1 * | 9/2002 | Bryan et al. | 623/17.15 |
| 2006/0085075 | A1 * | 4/2006 | McLeer | 623/17.12 |

OTHER PUBLICATIONS

"MTS 810 FlexTest™ Material Testing Systems", MTS Systems Corporation, Eden Prarie MN 5534402290, Sep. 2002.
http://www.instron.us/wa/applications/biomedical/orthopaedic/spine_prost.aspx, "Intervertebrel Disc Prosthesis", Instron Corporation, Norwood, MA 02062-2643, 1997-2006 (Aug. 4, 2006).
http://www.bose-electroforce.com/product.cfm?pid=36&tid=28, "Six Degree-of-Freedom Full Spine Simulator", Bose Corporation—ElectroForce Systems Group, Eden Prarie, MN 55344 (Aug. 4, 2006).
http://www.machina.hut/.fi/project/hip2001/, "Tribology of Prosthetic Joints", pp. 1-13, (Aug. 4, 2006).-
"The new ENDOLAB Spine Simulator", Endolab GmbH, D-83101 Thansau, Germany, pp. 1-2, (date unknown).
http:/www.simsol.co.uk/spine.shtml, Spinal Biomedical Fatigue Simulator, Simulation Solutions U.K., Stockport SK5 7DL, UK, pp. 1-2, (Aug. 4, 2006).
http:/etrs.org/bulletin10_1/section5.html, "Functional Tissue Engineering—University of Leeds, Professor John Fisher", European Tissue Repair Society, Bulletin 10.1, News from the Laboratory, pp. 1-2, (Aug. 4, 2006).

* cited by examiner

*Primary Examiner*—Max Noori
(74) *Attorney, Agent, or Firm*—Fay Sharpe LLP

(57) ABSTRACT

A single drive shaft simulator and method is disclosed that allows up to four independent actions to be imposed on a test specimen such as an artificial joint specimen. These motions about mutually orthogonal axes are provided, and a constant compressive force and/or dynamic force may also be applied. The mechanical simulator is simple, accurate, and robust. The simulator assures synchronous movement where amplitude and profiles of the motion can be independently adjusted.

31 Claims, 5 Drawing Sheets

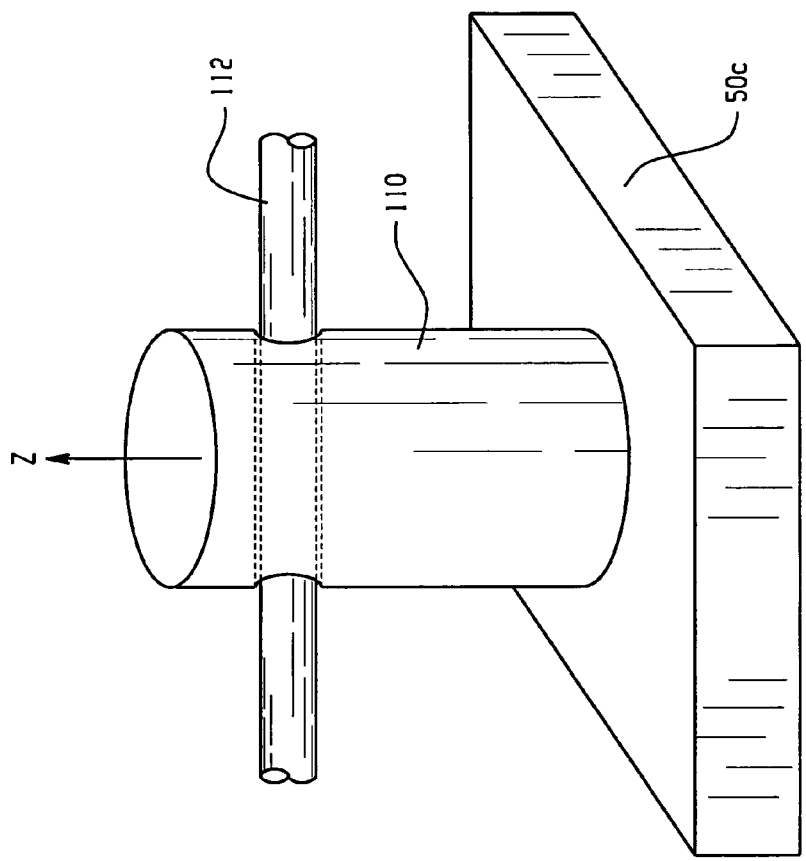
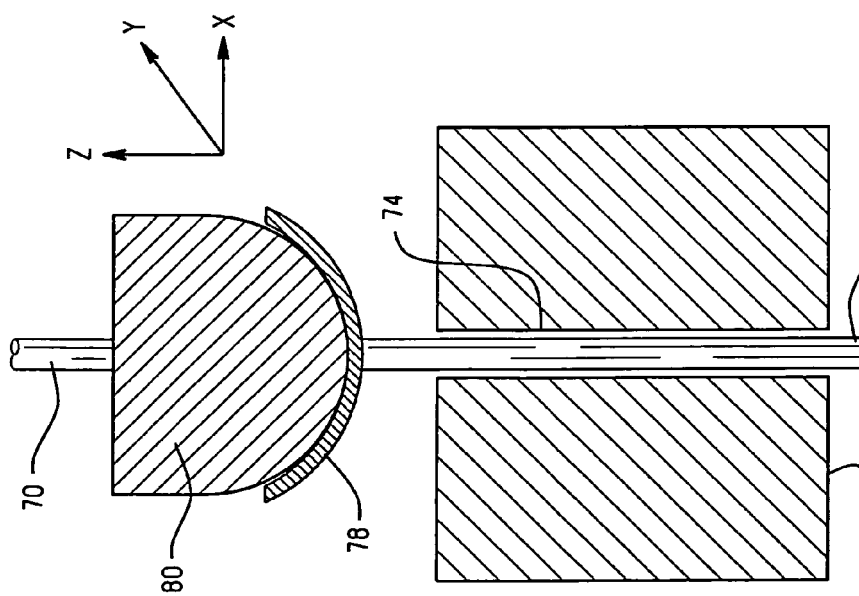

SIMULATOR FOR EVALUATING ARTIFICAL JOINT SPECIMENS AND ASSOCIATED METHOD

BACKGROUND OF THE INVENTION

This application relates to a simulator, particularly an apparatus and method of simulating or evaluating joint implants or artificial joints, for example, knee, spine, hip, and ankle joints, under simulated loading conditions. More particularly, the application relates to a mechanical simulator that is simple, accurate, and robust. However, features of the apparatus and method may be applicable to related uses that encounter the same or similar issues.

Artificial joints are prevalent and under continuous development and improvement. Just as important is the ability to test or simulate the artificial joint or implant under conditions that impose various loads representative of end use of the implant.

Commercially available simulators are relatively complex. For example, these units are typically servo-hydraulic units. However, these simulators are very expensive. Moreover, the servo-hydraulic simulators suffer drawbacks associated with their design. For example, the servo controls are electronic in nature and the lack of synchronous operation over an extended period of time can adversely impact test results. That is, separate servo controls are typically provided for separate motion of different axes. Trying to coordinate the separate motions over a large number of cycles (on the order of one to ten million cycles, for example) leads to the problem of the separate motions becoming out of synchronization.

As a result of the synchronization issue, or in an attempt to simplify and reduce the cost of the simulator, these known servo-hydraulic simulators often approximate the results of tests on specimens by adding the results from one set of motions to the other. For example, an implant may be exposed to cycling along one axis such as ten million cycles and then on a second axis in which the specimen has undergone another ten million cycles. The individual results are then mathematically superimposed in an effort to estimate the combined effects of the individual evaluations.

Still another issue with known simulators is that they are not as robust or rugged as desired. Multiple input sources are more prone to problems and not as desired as a single drive shaft.

Accordingly a need exists in the industry for a simulator that is accurate, robust, and versatile. The simulator must be able to provide a number of different types of motion, and able to maintain the desired synchronous movement even after an extended number of cycles. The ability to vary the different types of motion, e.g., vary the aspect ratio, is also a desired feature. There is also the need to expose the test specimen to static, compression, and dynamic forces while allowing motions about three orthogonal axes in a saline or bovine serum that approximates the end use of an implant, which may include the ability to vary the temperature at which the specimen is subjected. Further, the cost of the simulator must be reasonable in order to gain acceptance in the industry.

SUMMARY OF THE INVENTION

A single drive shaft simulator is provided that allows up to four independent actions to occur simultaneously while allowing motions about three orthogonal axes and the ability to apply dynamic, periodic, or static compressive forces to a test specimen.

A preferred apparatus for evaluating an associated artificial joint implant under simulated loading conditions includes a driver for providing an input motion, means for receiving the associated artificial joint implant and receiving the input motion from the driver, means for compressively loading the receiving means, and a selectively adjustable means for moving a first portion of the receiving means relative to a second portion of the receiving means.

A preferred embodiment of the apparatus includes a cavity filled with a fluid for immersing the associated artificial joint implant. The apparatus may also include means for controlling a temperature of the fluid, where the fluid is preferably one of a saline or bovine serum.

The moving means preferably includes means for adjusting at least one of an amplitude and profile of the relative motion.

The moving means at least partially rotates the first portion of the receiving means about a first axis relative to the second portion of the receiving means, and further includes means for at least partially rotating the first portion of the receiving means relative to the second portion of the receiving means about a second axis orthogonal to the first axis.

Another embodiment includes means for at least partially rotating the first portion of the receiving means relative to the second portion of the receiving means about a third axis orthogonal to the first and second axes.

The moving means may be selectively variable for altering an extent of movement.

The compressive loading means may be either dynamic or periodic.

BRIEF DESCRIPTION OF THE DRAWINGS

FIG. 4 is a cross-sectional view of a second preferred embodiment of the block of FIG. 2.

FIG. 6 is a schematic representation of selected components of the assembly associated with the z-motion.

DETAILED DESCRIPTION OF THE PREFERRED EMBODIMENTS

Figure 1:
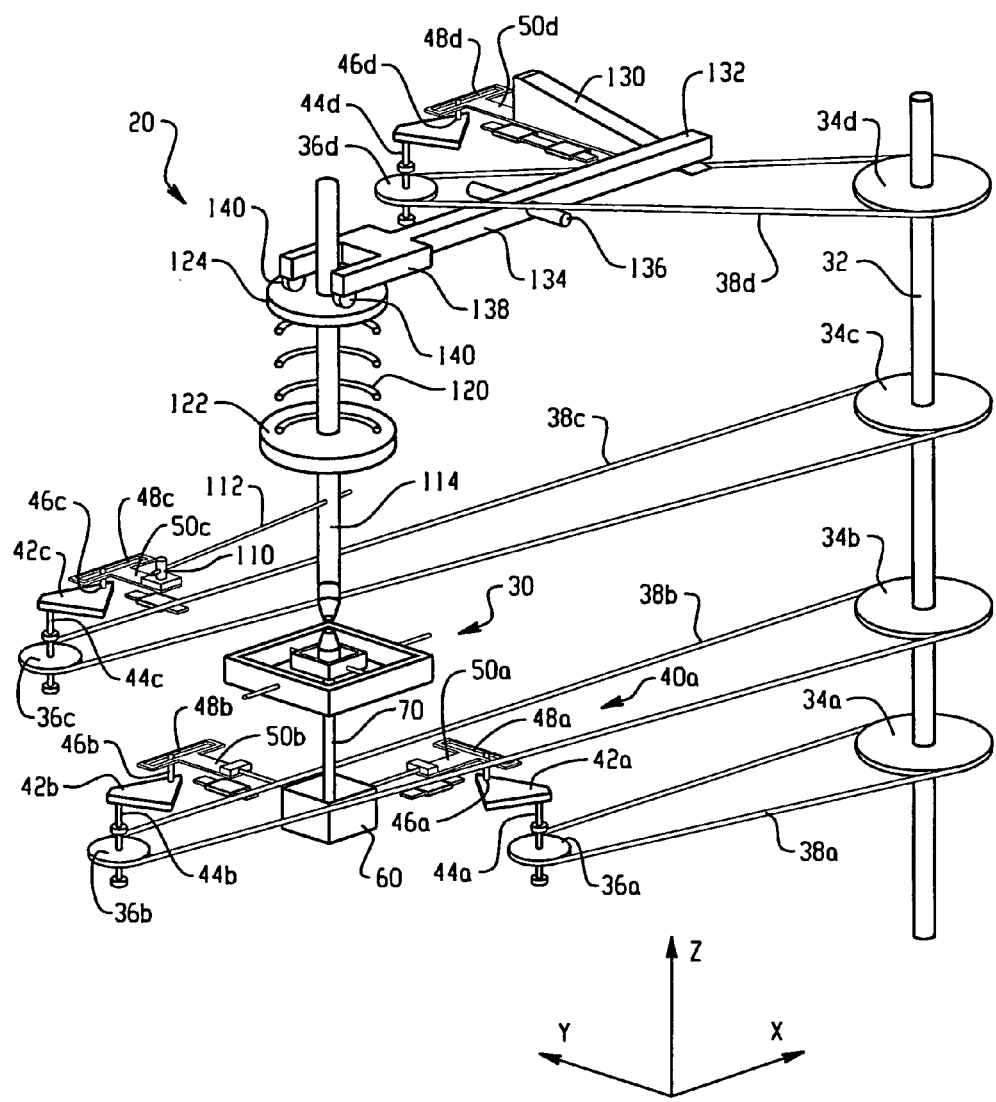
FIG. 1 is an isometric, schematic view of a first preferred embodiment of a simulator assembly.

Turning initially to FIG. 1, there is illustrated a preferred embodiment of a simulator 20 for testing a specimen (not shown) for a preselected number of cycles. More specifically, the simulator includes a test chamber or nested gimbal 30 that provides a means for receiving a specimen (not shown) in a cavity thereof for testing artificial implants, for example, for wear and integrity along three orthogonal axes of relative motion (referenced here as orthogonal directions x, y, and z). It will be appreciated that the same device can also be used to conduct wear and integrity tests of specimens along dual axes or a single axis by simply disabling one or more of the means for generating motion along selected axes. These motions are infinitely adjustable in both amplitude and profile in a convenient, and preferably periodic. Moreover, the motion associated with each axis is adjustable independently of the motion of the other axes.

In addition, forces may be applied to the specimens along one of the axes (here, the z axis). This force is preferably a compressive force that may be constantly applied or dynamic (e.g., periodically applied). Further, the compressive force may be easily adjusted.

Advantageously, all of these actions, that is, four primary actions (three axes of motion and the application of a constant or dynamic force) are achieved through use of a single drive, namely a drive shaft 32. The drive shaft 32 is driven by a motor (not shown) and has separate pulleys 34 fixed thereon for rotation with the drive shaft. These drive pulleys 34 may be the same size, or different sizes, depending on the particular needs of the testing to be conducted on the specimen. The drive pulleys are axially spaced along the shaft and are intended to provide a drive force to a driven pulley 36 through an associated belt 38 necessary for an individual action. For ease of understanding and description, each drive pulley will be identified by reference numeral 34 along with an associated reference letter that correlates to a particular action (identified generically as actions a-d), the associated driven pulley will be identified by reference numeral 36 with the corresponding reference letter a-d, and similarly the belt will be identified by reference numeral 38 with the corresponding reference letter a-d. However, it will be understood by one skilled in the art that such identification or order of description herein should not be deemed limiting, and that these assemblies may be generally referred to as means for moving one portion of the receiving means (test chamber) relative to another portion. Thus, for example, drive pulley 34a cooperates with a corresponding driven pulley 36a through belt 38a to provide for motion along the x-axis as will be detailed below. This, in turn, generates a rotary motion about the y-axis, again as will be described further below. It will also be appreciated that the belts and pulleys are not the only type of mechanism that is capable of effectively transferring motion from a single drive (shaft 32) to create multiple actions, however, this is a simple, effective mechanism that is used in a preferred embodiment of the invention. It also advantageously assures synchronization among the various actions.

Figure 2:
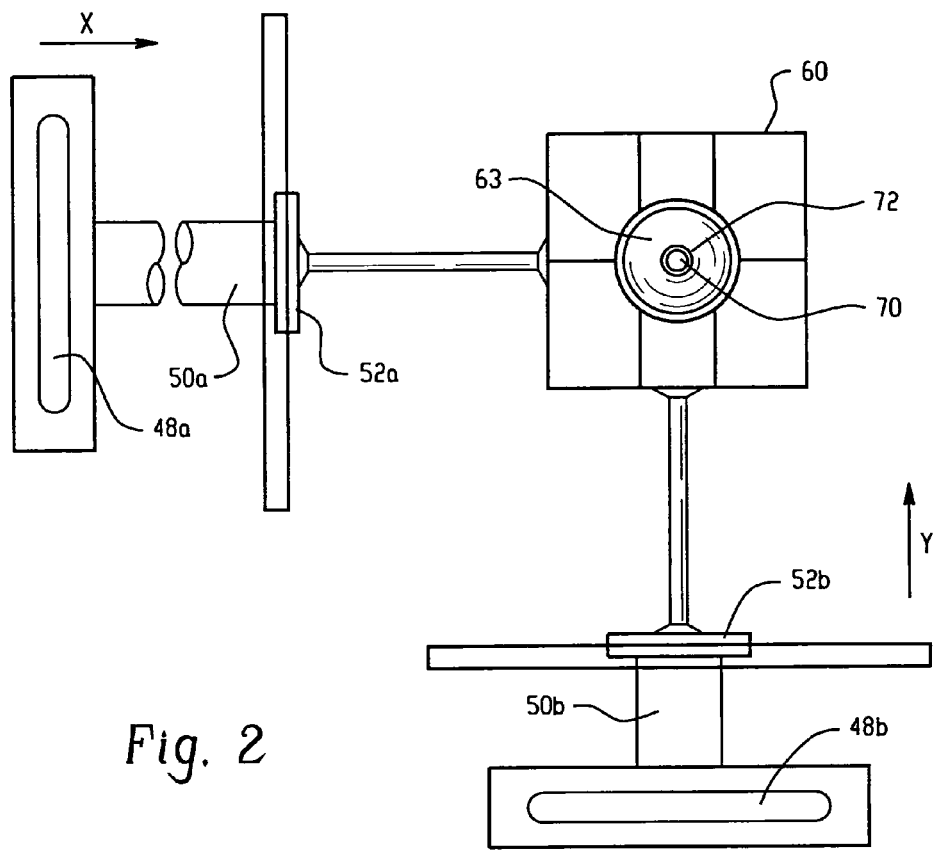
FIG. 2 is a top plan view of the block associated with x-y motion of the specimen.

The driven pulley 36a rotates a rotary-to-linear conversion mechanism shown here as a scotch yoke mechanism 40. Particularly, the scotch yoke mechanism 40 includes a rotary member, or in this instance a wedge-shaped member 42, that rotates with the driven pulley. That is, the driven pulley 36a and the rotary member 42a are mounted on the same shaft 44 for common rotation. The rotary member 42a includes a pin 46a that extends outwardly therefrom and is received in a corresponding slot 48a of a linear member, or T-shaped component, 50a of the scotch yoke mechanism. The T-shaped component 50a is limited to travel along a rail 52 (FIG. 2) that guides the T-shaped component 50a in the x-direction. Thus, the action of the scotch yoke mechanism is a sinusoidal output.

Figure 3:
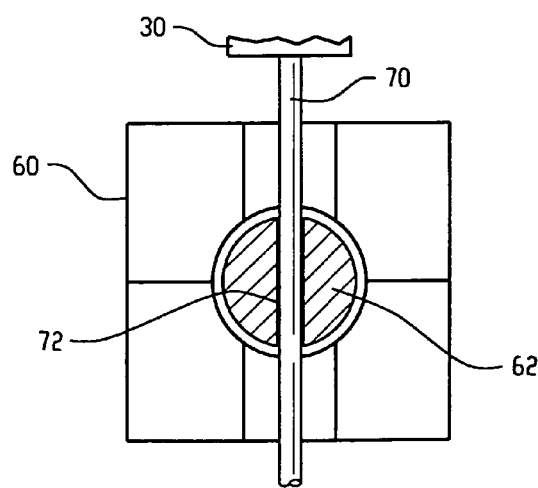
FIG. 3 is a cross-sectional view of a first preferred embodiment of the block of FIG. 2.

An output end 54 of the T-shaped component is operatively secured to an x-y block 60. More specifically, the x-y block 60 is shown in greater detail in FIG. 3. A spherical or ball member 62 is received in the block and may rotate relative to the block in response to motion of the block in the x-y directions. A rod 70 extends through an opening 72 the ball member 62 and has one end 64 that connects to the test chamber 30. Thus, as the x-y block is moved along the x-axis in response to rotation of drive pulley 32a, the rod exerts a moment or rotary motion on the test chamber. As will be appreciated, the rotary motion is about the y-axis as a result of the motion of the T-shaped member 50a traveling along the x-axis.

A second drive pulley 34b is connected to the drive shaft 32. The second drive pulley 34b rotates driven pulley 36b via the belt 38b which, in turn, rotates wedge-shaped member 42b of a second rotary-to-linear or scotch yoke mechanism 40b. A second linear component or T-shaped member 50b translates in the y-direction in response to rotation of the wedge-shaped member 42b. Here, the translation in the y-direction results in rotary motion of the test chamber about the x-axis as the output end 54b of the T-shaped member is secured to the x-y block 60, and thus connected to the nested gimbal arrangement or test chamber via rod 70.

An alternative structure for the x-y block and the ball member is shown in FIG. 4. Specifically, rather than incorporating a ball member into an internal cavity of the x-y block, an elongated opening 74 is provided in the block and receives a lower rod portion 76 that has a hemispherical end 78 dimensioned to receive hemispherical end 80 on the end of the rod 70 that extends to the test chamber. The mating conformation of the hemispherical ends 78, 80 allow the travel or action of the T-shaped members to be conveyed to the test chamber.

Figure 5:
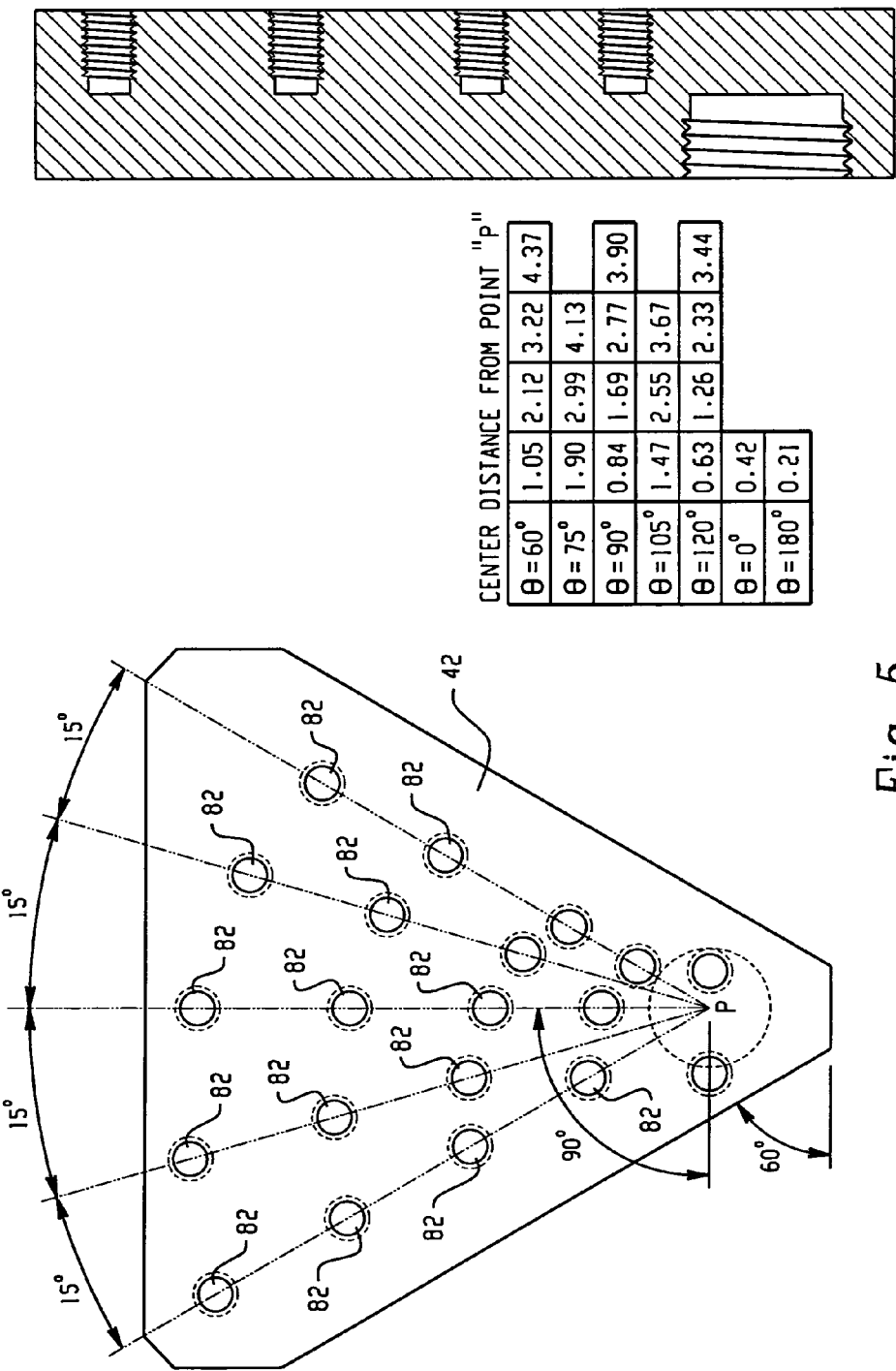
FIG. 5 is a plan view of one component of a scotch yoke assembly.

The x and y rotary motions imposed on the test specimen housed in the chamber 30 are generally shown to be the same. That is, the size of the drive pulleys 34a, 34b and the driven pulleys 36a, 36b are shown as being the same, however, one skilled in the art will appreciate that the sizes may be different, or the location of the pin on the wedge shaped members 42a, 42b may be varied in order to alter the output. For example, a representative rotary member is shown in FIG. 5. Numerous openings or recesses 82 are provided in the rotary member and are similarly sized for receipt of the pin (not shown in FIG. 4). Depending on the location of the pin relative to point P which is representative of the location of the shaft 44, the linear output or motion of the scotch yoke is altered. In this way, the stroke of the T-shaped member associated with the rotary-to-linear converter may be easily adjusted. This provides a seemingly infinite variety of outputs that can be achieved with the simulator, and still assures that the action of the different rotary-to-linear actuators is synchronized since the same, single source of drive motion (drive shaft 32) is used. The angular extent may be varied as noted by the arcs of 60, 75, 90, 105 and 120 degrees, and likewise the amplitude may be varied depending on the distance from the point P.

The test specimen in test chamber 30 is subjected to the rotary motion imposed by the pair of rotary-to-linear converters 40a, 40b. The external framework 90 of the test chamber includes a first frame member 92 that is adapted to rotate about support axis 94 and similarly the second frame member 96 is adapted to rotate about the support axis 98. Thus, the rotational motion imposed through the rod 70 from the first and second rotary-to-linear converters is transferred to the test specimen since the frame members are adapted to rotate about their respective support axes.

Rotation of the test specimen about a third orthogonal axis (z-axis) is also provided by the preferred embodiment of FIG. 1. As will be appreciated, the third drive pulley 34c is connected to the single drive shaft 32. The rotary motion is transferred to the driven pulley 36c by the belt 38c, and the wedge-shaped rotary member 42c also rotates as a result of being commonly mounted on shaft 44c with the driven pulley. The pin 46c fixed to the wedge-shaped member imparts reciprocating motion to the T-shaped member via slot 48c. The operation of the third means for imparting motion to the test specimen may be adjusted by altering the size of the drive or driven pulleys, or repositioning the pin 46c on the wedge-shaped rotary member in the same manner as described with respect to the x and y axes moving means 40a, 40b.

As is apparent, so far the description of the third means for moving one portion of the test chamber relative to another portion is identical to that described and shown with respect to the structure and function of the x and y axes. Here, however, the z axis assembly is slightly altered by incorporating a freely rotating cylinder 110 on the T-shaped member that has a transverse opening that freely receives stem 112. The stem is secured at an opposite end to an upper rod 114 that is operatively associated with the test chamber so that as the T-shaped member is reciprocated, the cylinder will rotate and pivots the upper rod back and forth about the z-axis. This rotary motion about the z-axis is conveyed to the test specimen in the test chamber via upper rod 114.

In this manner, the simulator provides for three rotary motions to be imparted to the test specimen, each of which is driven by a single drive source, and each of which is independently adjustable relative to one another. By using the single drive source, synchronization is assured and the simple mechanical structures are durable and sufficiently robust to withstand a large number of cycles.

With continued reference to FIG. 1, the test specimen may also be loaded in compression by incorporating a load spring 120. Particularly, the load spring 120 is received between a pair of spaced apart plates 122, 124 secured to the upper rod 114. The spring is place in compression and thus imparts a compressive force on the test specimen. This load may be a static load, for example, applying a load on the order of 30N to 3500N.

Alternatively, the compressive load may be made dynamic and periodic by including an additional means for imparting action/motion to the test specimen. As shown in FIG. 1, the fourth mechanism includes a fourth drive pulley 34d that operates a fourth driven pulley 36d via belt 38d. Once again, a scotch yoke mechanism is preferably used and the wedge-shaped rotary member 42d thereof is adapted to rotate with shaft 44d. Pin 46d extends outwardly from the rotary member and is received in slot 48d of the T-shaped linear operating member 50d. Thus as described with respect to the other three scotch yoke mechanisms, the amplitude and profile of the motion may be selectively adjusted by changing the sizes of the pulleys and/or the location of the pin. In this instance, the operation is further changed by adding an inclined surface 130 that cooperates with one end 132 of a lever 134 that pivots about fulcrum 136. The opposite end 138 of the lever includes a forked configuration having rollers 140 on the underside thereof that are adapted for sliding or rolling receipt on an upper surface of the second plate 124. As the T-shaped member 50d reciprocates, the inclined surface raises and lowers the first end 132 of the lever 34 which raises and lowers the second end 138 as the lever pivots about the fulcrum. This provides a dynamic and periodic application of force (in addition to the spring force, if so desired). It will be understood that the profile of this dynamic force application can also vary widely dependent on the shape, for example, of the inclined surface. Likewise, this is one way of providing a dynamic, periodic force application to the test specimen and the invention should not be limited to this particular exemplary embodiment.

The test specimen may also be housed within a non-corrosive fluid such as a saline or bovine solution. This is represented by dashed line 150 in FIG. 1. Control box 152 is representative of the ability to selectively control the temperature of the fluid in which the test sample is immersed. A temperature controller of conventional construction may be incorporated into the simulator to control the temperature between about −20 degrees to 20 degrees Celsius during testing, or alternatively to maintain the test sample near ambient to 50 degrees Celsius.

It will be appreciated that the present arrangement allows the setup to vary the testing of the sample. For example, the relative phasing among the x, y, and z motions may be altered from one test to another. The x, y, and z motions may be set to remain phase constant or adjusted among one another as required for different testing conditions.

The described simulator allows evaluation of an artificial joint implant for wear and integrity under simulated in-vivo loading conditions. This is achieved with a durable, adjustable electromechanical system that is relatively low cost. The simulator can be used as a single axis test device to test artificial implants for their wear and structural integrity along one axis of relative motion between the implant stems or other fixation points. A constant prescribed compressive force is applied to the stems of the implants during the tests. The relative motion between the stems of the implant is periodic, with the amplitude and profile of this motion being adjustable.

Alternatively, the simulator can be used as a dual axes test device to test artificial implants for their wear and structural integrity along two orthogonal axes of relative motion between the implant stems or other fixation points. A constant compressive force is applied to the stem of the implants during the tests. The relative motions between the stems of the implant, along the two orthogonal axes are periodic, with the amplitudes and profiles of these motions being independently adjustable.

Yet another alterative is a tri-axes test device to test artificial implants for their wear and structural integrity along three orthogonal axes of relative motion between the implant stems or other fixation points. A constant compressive force is applied to the stems of the implants during the tests. The relative motions between the stems of the implant, along with three (3) orthogonal axes are periodic, with the amplitudes and profiles of these motions being independently adjustable.

A single-axis test device to test artificial implants for their wear and structural integrity along one axis of relative motion between the implant stems or other fixation points is a further alternative. A dynamic, periodic compressive force is applied to the stems of the implants during the tests. The amplitude of this periodic force is adjustable. The relative motion between the stems of the implants is periodic, with the amplitude and profile of this motion being adjustable.

A dual-axes test device to test artificial implants for their wear and structural integrity along two orthogonal axes of relative motion between implant stems or other fixation points is still another alternative. A dynamic, periodic compressive force is applied to the stems of the implants during the tests. The amplitude of this periodic force is adjustable. The relative motions between the stems of the implant, along the two orthogonal axes are periodic, with the amplitudes and profiles of these motions being independently adjustable.

A tri-axes test device to test artificial implants for their wear and structural integrity along three orthogonal axes of relative motion between the implant stems or fixation points is yet another alternative. A dynamic, periodic compressive force is applied to the stems of the implants during the tests. The amplitude of this periodic force is adjustable. The relative motions between the stems of the implant, along three (3) orthogonal axes are periodic, with the amplitudes and profiles of these motions being independently adjustable.

Further, the shape of this dynamic and periodic compressive force as a function of time is adjustable. There is a single drive shaft that drives all of the axes of motion and the dynamic and periodic force to the stems of the artificial implant. Use of a single drive shaft for the four actions, namely, three axes of motion and the application of the dynamic force, guarantees a chosen synchronous motion among the four actions. Specimens may be evaluated at ambient temperature or elevated and controlled temperatures while submerged in non-corrosive liquid.

Figure 7:
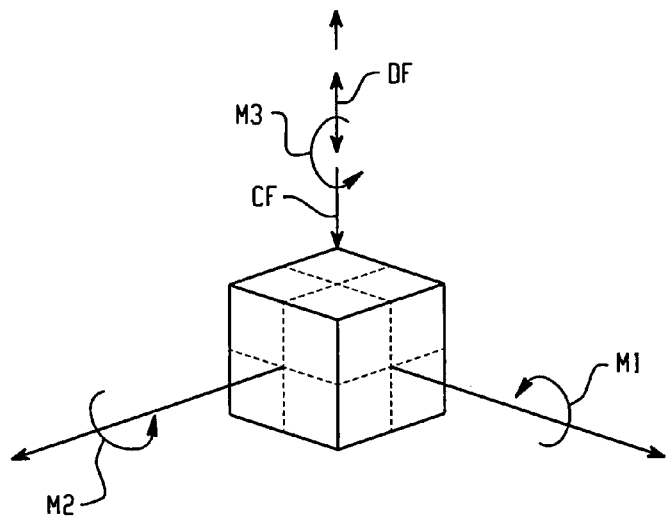
FIGS. 7 and 8 are schematic illustrations of the test specimens showing the three axes of motion (partial rotation) as well as the applied static or dynamic load.
Figure 8:
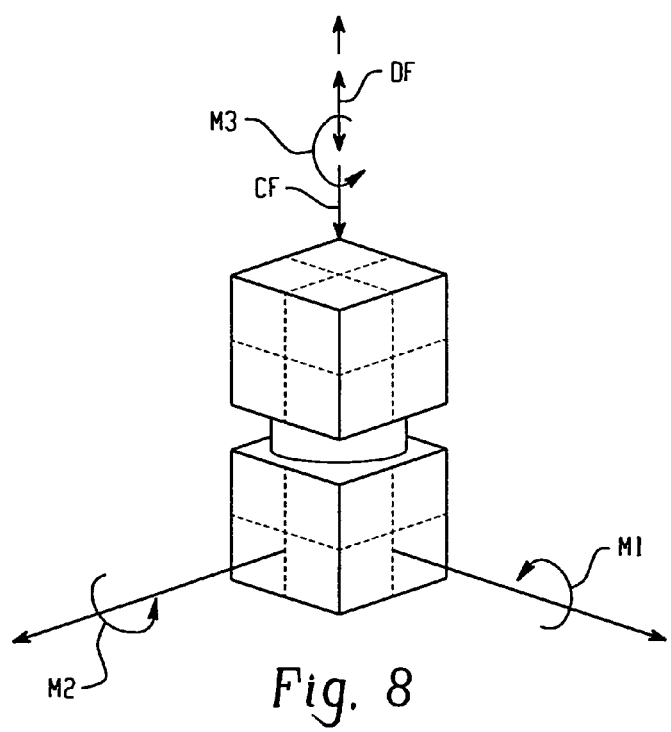

The test structures described above are schematically shown in FIGS. 7 and 8. The specimen is received in a test chamber and relative motion M1, M2, M3 may be imposed on the test specimen on at least one of the three orthogonal axes. In addition, a constant compressive force CF and/or dynamic force DF may also be applied to the specimen as represented in these figures.

Preferred values and variable are as follows:
Temperature: ambient to 50° C.
Frequency: 0 to 4 Hz.
A single-axis test: 1.) –20° to 20° C., 30N to 3500N static compressive.
A dual-axes test: 1.) –20° to 20° C.; 2.) –20° to 20° C., 20N to 3500N static compressive.
A tri-axes test: 1.) –20° to 20° C.; 2.) –20° to 20° C.; and 3.) –20° to 20° C., 20N to 3500N static compressive.
A single-axis test: 1.) –20° to 20° C., 30N to 3500N dynamic, periodic compressive.
A dual-axes test: 1.) –20° to 20° C.; 2.) –20° to 20° C., 20N to 3500N dynamic, periodic compressive.
A tri-axes test: 1.) –20° to 20° C.; 2.) –20° to 20° C.; and 3.) –20° to 20° C., 20N to 3500N dynamic, periodic compressive.
Preferred specimen size not to exceed 15 cm wide by 15 cm deep by 25 cm high.
Preferred radii of motion should not exceed 10 cm.

Due to the overall size of the simulator frame, more than one testing chamber may be accommodated within the space.

The invention has been described with reference to the exemplary embodiments. Obviously, modifications and alterations will occur to others upon reading and understanding the preceding detailed description. It is intended that the invention be construed as including all such modifications and alterations.

Having thus described the invention, it is now claimed:

1. An apparatus for evaluating an associated artificial joint implant under simulated loading conditions, the apparatus comprising:
   a driver for providing an input motion;
   a receiver that receives the associated artificial joint implant and receives the input motion from the driver;
   a first mechanism compressively loading the receiver in a cyclic fashion; and
   a second mechanism that moves a first portion of the receiver relative to a second portion of the receiver, the second mechanism being selectively adjustable, wherein second mechanism at least partially rotates the first portion of the receiver about a first axis relative to the second portion of the receiver and further comprising a member that rotates the first portion of the receiver relative to the second portion of the receiver about a second axis orthogonal to and independent of the rotating member about the first axis, wherein the first and second axes are synchronously driven.

2. An apparatus for evaluating an associated artificial joint implant under simulated loading conditions, the apparatus comprising:
   a driver for providing an input motion;
   means for receiving the associated artificial joint implant and receiving the input motion from the driver, wherein the receiving means includes a cavity filled with a fluid for immersing the associated artificial joint implant;
   means for compressively loading the receiving means in a cyclic fashion; and
   means for moving a first portion of the receiving means relative to a second portion of the receiving means, the moving means being selectively adjustable.

3. The apparatus of claim 2 wherein the rotation about the first axis extends over approximately 40 degrees.

4. The apparatus of claim 2 wherein the moving means at least partially rotates the first portion of the receiving means about a first axis relative to the second portion of the receiving means.

5. The apparatus of claim 2 wherein the receiving means includes means for controlling a temperature of the fluid.

6. The apparatus of claim 5 wherein the temperature ranges between ambient to 50 degrees C.

7. The apparatus of claim 2 wherein the fluid is one of a saline or bovine serum.

8. The apparatus of claim 2 wherein the moving means includes means for adjusting at least one of an amplitude and profile of the relative motion.

9. An apparatus for evaluating an associated artificial joint implant under simulated loading conditions, the apparatus comprising:
   a driver for providing an input motion;
   means for receiving the associated artificial joint implant and receiving the input motion from the driver;
   means for compressively loading the receiving means; and
   means for moving a first portion of the receiving means relative to a second portion of the receiving means, the moving means being selectively adjustable, wherein the moving means at least partially rotates the first portion of the receiving means about a first axis relative to the second portion of the receiving means, and further comprises means for at least partially rotating the first portion of the receiving means relative to the second portion of the receiving means about a second axis orthogonal to the first axis.

10. The apparatus of claim 9 further comprises means for at least partially rotating the first portion of the receiving means relative to the second portion of the receiving means about a third axis orthogonal to the first and second axes.

11. The apparatus of claim 10 further comprising means for translating the first portion of the receiving means relative to the second portion of the receiving means.

12. The apparatus of claim 11 wherein the translating means imparts translational movement in a direction substantially perpendicular to a directional axis of the compressive loading means.

13. The apparatus of claim 2 further comprising means for translating the first portion of the receiving means relative to the second portion of the receiving means.

14. The apparatus of claim 2 wherein the moving means is selectively variable for altering an extent of movement.

15. The apparatus of claim 2 wherein the receiving means is dimensioned to receive an associated spheroidal artificial joint implant.

16. The apparatus of claim 2 further comprising means for counting movement of the receiving means first portion relative to the second portion.

17. An apparatus for evaluating an associated artificial joint implant under simulated loading conditions, the apparatus comprising:

a driver for providing an input motion;

a receiver that receives the associated artificial joint implant and receives the input motion from the driver;

a first mechanism compressively loading the receiver in a cyclic fashion;

a second mechanism that moves a first portion of the receiver relative to a second portion of the receiver, the second mechanism being selectively adjustable;

a first rotational drive mechanism at least partially rotating the first mechanism of the receiver about a first axis relative to the second mechanism of the receiver and further comprising a second rotational drive mechanism that rotates the first portion of the receiver relative to the second portion of the receiver about a second axis orthogonal to and independent of the first rotational drive mechanism about the first axis.

18. The apparatus of claim 17 wherein the first rotational drive mechanism and the second rotational drive mechanism are commonly driven.

19. The apparatus of claim 17 further comprising a third rotational drive mechanism that rotates the first portion of the receiver about a third axis orthogonal to and independent of the first and second axes.

20. The apparatus of claim 19 wherein the first, second and third rotational drive mechanisms are commonly driven.

21. The apparatus of claim 19 further comprising a first translational mechanism that translates the first portion of the receiver relative to the second portion of the receiver 22. The apparatus of claim 21 wherein the first translational mechanism imparts translational movement in a direction substantially perpendicular to a directional axis of the first mechanism.

23. The apparatus of claim 2 wherein the compressive loading means is dynamic.

24. The apparatus of claim 23 wherein the compressive loading means is periodic.

25. The apparatus of claim 2 wherein the compressive loading means ranges from about 30N to about 3500N.

26. An apparatus for dynamically evaluating an associated artificial joint implant under simulated loading conditions, the apparatus comprising:

a receiver having first and second relatively movable portions dimensioned to receive an associated joint implant therebetween; and a single driver for moving the first portion relative to the second portion in four independent actions.

27. The apparatus of claim 26 wherein three of the four independent actions are motion about three orthogonal axes.

28. The apparatus of claim 27 wherein the fourth independent action is a translational motion.

29. The apparatus of claim 27 wherein the fourth independent action is a compressive force application.

30. The apparatus of claim 29 wherein a force application mechanism applies a constant compressive force between the first and second portions of the receiver.

31. The apparatus of claim 29 wherein a force application mechanism applies a periodic compressive force between the first and second portions of the receiver.

* * * * *